United States Patent [19]

Chastain et al.

[11] Patent Number: 5,110,832
[45] Date of Patent: May 5, 1992

[54] USING PERILLYL ALCOHOL TO KILL BACTERIA AND YEASTS

[75] Inventors: Doyle E. Chastain, 137 Birch St., Titusville, Fla. 32780; W. Eugene Sanders, Jr.; Christine C. Sanders, both of Omaha, Nebr.

[73] Assignee: Doyle E. Chastain, Titusville, Fla.

[21] Appl. No.: 597,488

[22] Filed: Oct. 9, 1990

[51] Int. Cl.$^5$ .................. A01N 31/00; A61K 31/045
[52] U.S. Cl. .................................................. 514/729
[58] Field of Search ........................................ 514/729

[56] References Cited

U.S. PATENT DOCUMENTS 3,595,975  7/1971  Gavreau ........................ 514/179

FOREIGN PATENT DOCUMENTS 981695   1/1976  Canada.
1077959  5/1980  Canada.

OTHER PUBLICATIONS

A. Bardyshev Chem. Abs. 80 (1974), 359.
B. Murdock and Allen, Food Technology 14 (No. 9, 1960) 441-5.
C.A.; Kurita et al., vol. 94 (1981) 94:186,166c.
Blumann et al., vol. 63 (1965) 1819 d.

*Primary Examiner*—Allen J. Robinson
*Attorney, Agent, or Firm*—Arthur G. Yeager

[57] ABSTRACT

A broad spectrum bactericide, which is bactericidal to bacteria and yeasts in bactericidal concentrations, is perillyl alcohol. Also a method of killing bacteria includes the treatment of bacteria with bactericidal concentrations of perillyl alcohol. The bacteria are selected from a goup consisting of Staphylococcus, Billus, Enterobacteriaceae, Streptococcus, Xanthomonas, and Mycobacteria. Also yeasts may be killed by treatment thereof with bactericidal concentrations of perillyl alcohol.

3 Claims, No Drawings

USING PERILLYL ALCOHOL TO KILL BACTERIA AND YEASTS

TECHNICAL FIELD

The object of this invention is to demonstrate a method of using perillyl alcohol to kill bacteria and yeasts.

BACKGROUND OF THE INVENTION (1) Field of the Invention

During the study of limonene as a hand cleaner, the applicants found that fully oxygenated limonene is a bactericide. A review of the literature revealed that oxygenated limonene contains several oxidation products including: cis and trans-carveol, trans-p-menth-8-ene-1,2-diol, limonene 1,2-epoxide, limonene 8,9-epoxide, cis and trans-p-mentha-2,8-dien-1-ol, and perillyl alcohol, as was outlined by Blumann in Chemical Abstracts, Volume 63, 1965, on page 1819. The applicants found that a principal bactericide generated by the oxidation of limonene is perillyl alcohol which, in bactericidal concentrations, kills bacteria and yeasts.

Perillyl alcohol is a monocyclic monoterpene similar to limonene. Limonene is not bactericidal. Their chemical formulas follow below.

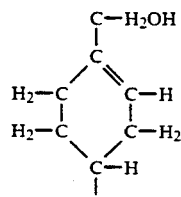
Perillyl Alcohol

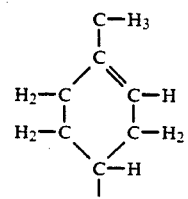
Limonene

It should be noted that the formula for perillyl alcohol is identical to the formula for limonene with the exception of a hydroxyl group which replaces a hydrogen atom at carbon 7. Because limonene is not bactericidal, the exchange of a hydroxyl group for a hydrogen atom at carbon 7, was not expected to make the resulting compound (perillyl alcohol) bactericidal. All other monocyclic monoterpenes terpenes that have known bactericidal activity are similar to limonene, but have a hydroxyl group or an oxygen atom replacing a hydrogen atom on the benzene ring at carbons 2, 3, 4 or 8 (as opposed carbon 7, 9, or 10) that is appreciated in the structures of: carveol, carvone, hydrocarveol, hydrocarvone, pulegone, isopulegol, menthol, menthone, terpinen-4-ol, and a-terpineol which follow. None of the monocyclic monoterpenes that have bactericidal activity have a hydroxyl group at the carbon 7, 9, or 10 position.

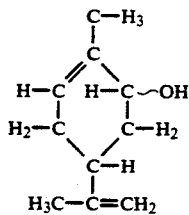
Carveol

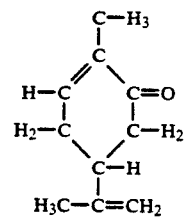
Carvone

-continued

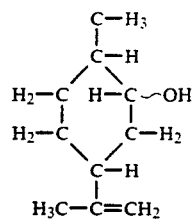
Dihydrocarveol

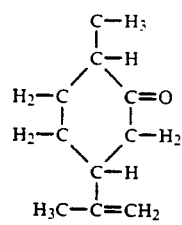
Dihydrocarvone

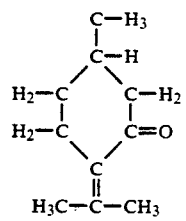
Pulegone

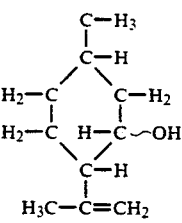
Isopulegol

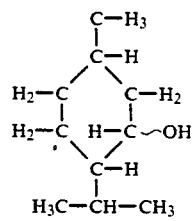
Menthol

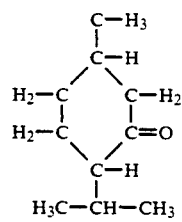
Menthone

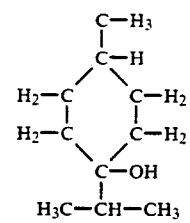
Terpinen-4-ol

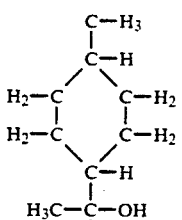
a-Terpineol

Although it was not expected, the applicants were totally surprised to find that perillyl alcohol is bactericidal to bacteria and yeasts.

Perillyl alcohol is an oil with a terpenic aroma. It is insoluble in water, is poorly soluble in propylene glycol, and is almost insoluble in glycerine. Perillyl alcohol is soluble in alcohol and is miscible in oil. It is used as a flavoring agent for cosmetics and perfumes, but heretofore, it has not been used as a bactericide. Perillyl alcohol can be produced by the oxidation of limonene as was demonstrated by Blumann in Chemical Abstracts, Volume 63, 1965 on page 1819, and Bardychev in Chemical Abstracts, Volume 80, 1974, page 359. It can be produced by the acetylation of limonene as described by Ansari, Hifzure R. (German Offen 2,513,910 and Canadian Patent No. 1,077,959). Walling made perillyl alcohol (Canadian Patent No. 981,695) from beta pinene by adding benzyl peroxide to beta pinene followed by alkaline hydrolysis to perillyl alcohol.

(2) Description of the Prior Art

Zukerman studies the effect of auto-oxidized d-limonene on bacteria, but found it was weakly bacteriostatic, was unstable, and lost its bacteriostatic effect on keeping as was discussed in Nature 169:517 (1951). He never studied perillyl alcohol. Kurita investigated the fungicidal activity of several components of essential oils as was reported in Biol. Chem., 45(4), 945-952, 1981, but he never studied the bactericidal activity of perillyl alcohol against bacteria nor yeasts. Murdock and Allen showed that the germicidal effect of sodium benzoate against yeasts was enhanced by the orange peel oil and d-limonene, as was outlined in Food Technology, Vol. 14, No. 9, 1960, pages 441-5. They never studied the antimicrobial activity of perillyl alcohol against bacteria nor yeasts. Kellner et al demonstrated that several ethereal oils and some of their constituents have antimicrobial activity as was reported in Arneimittel-Forschung, 5, 224-9, 1955. He confirmed that limonene is not bactericidal. He never studied perillyl alcohol for bactericidal activity. Gauvreau showed a means of producing disinfecting compositions in U.S. Pat. No. 3,595,975 by combining cetyl pyridinium hydrochloride with terpenes to form antiseptics, but he never studied the use of perillyl alcohol alone nor in combination with cetyl pyridinium hydrochloride. The active ingredient in his disinfecting compositions was cetyl pyridinium hydrochloride (and not the terpenes). A. Morel revealed the sterilizing action of carveol, dihydrocarveol, and their ozonization productions in Comp. Rend. Soc. Biol. Volume 115, pages 536-8 (1934). He never studied the bactericidal effect of perillyl alcohol.

It should be pointed out that drugs which are bactericidal are usually not fungicidal, and drugs which are fungicidal are usually not bactericidal In addition, drugs which are bactericidal frequently promote the growth of yeasts. Table A, which follows, exemplifies the bactericidal and fungicidal activity of several commonly used antibacterial, antiyeast, and antifungal antibiotics.

TABLE A

| ANTIBIOTICS | ANTIBIOTIC ACTIVITY AGAINST | | | | |
|---|---|---|---|---|---|
| | Gm + Bact | Gm − Bact | A F Bact | Yeast | Fungi |
| A. Anti-bacterial | | | | | |
| 1. Ampicillin | Y | Y | N | N | N |
| 2. Cephalothin | Y | Y | N | N | N |
| 3. Chloramphenicol | Y | Y | N | N | N |
| 4. Erythromycin | Y | N | N | N | N |
| 5. Ethambutol | N | N | Y | N | N |
| 6. Gentamicin | Y | Y | N | N | N |
| 7. Isoniazid | N | N | Y | N | N |
| 8. Nitrofurantoin | N | Y | N | N | N |
| 9. Penicillin | Y | N | N | N | N |
| 10. Rifampin | Y | N | Y | N | N |
| 11. Streptomycin | Y | Y | Y | N | N |
| 12. Sulfonamides | N | Y | N | N | N |
| 13. Tetracycline | Y | Y | N | N | N |
| 14. Vancomycin | Y | Y | N | N | N |
| B. Anti-Fungal | | | | | |
| 1. Chlotrimazole | N | N | N | Y | Y |
| 2. Griseofulvin | N | N | N | N | Y |
| C. Anti-Yeast | | | | | |
| 1. Nystatin | N | N | N | Y | N |
| 2. Gentian Violet | N | N | N | Y | N |

Gm + Bact = Gram Positive Bacteria, Gm − Bact = Gram Negative Bacteria, A F Bact = Acid Fast Bacteria, Y = Kills Organism, N = No Activity Against Organism It should be noted in the table above that none of the antibacterial antibiotics kill fungi, and none of the antifungal nor anti-yeast antibiotics kill bacteria. Thus, an antifungal antibiotic is not expected to kill bacteria and a antibacterial antibiotic is not expected to kill fungi or yeasts. Antifungal antibiotics do not necessarily kill yeasts and anti-yeast antibiotics do not necessarily kill fungi.

DISCLOSURE OF THE INVENTION

This invention relates to the use of perillyl alcohol as a bactericide. Perillyl alcohol is an oil which is available commercially, but heretofore, it has not been recognized as a bactericide. It is slightly viscous and when applied, readily adheres to glass, metal, wood, cloth, rope, book covers, paper, paint, cement, ceramics, plastic, plant surfaces, skin, mucus membranes, and teeth leaving an oily film. Because it is not soluble in water, its' adherence to surfaces allows prolonged exposure and makes perillyl alcohol an ideal bactericide against bacteria and yeasts regardless of whether they infect plants animals or humans.

The exact method of killing bacteria and yeasts is unknown, but it is thought that perillyl alcohol kills bacteria and yeasts by lysing the cell membrane of the organisms which is lethal to the organisms.

In practice, any surface, on which it is desirable to kill or prevent the growth of bacteria and yeasts, is treated with bactericidal concentrations of perillyl alcohol by swabbing, wiping, painting, washing, brushing, spraying, or any other direct application technique. Alternatively, perillyl alcohol can be incorporated in creams, ointments, tinctures, gels, suppositories, paints, sprays, aerosols, toothpastes, solutions, emulsions, soaps, scrubs, mouthwashes, or antiseptics, and applied anywhere it is desirable to kill or prevents the growth of bacteria and yeasts.

BEST MODE FOR CARRYING OUT THE INVENTION

The following examples are illustrative of the best mode of carrying out the invention. They are, obviously, not to be construed as limitative of the invention since various other embodiments can be readily evolved in view of the teachings provided herein.

EXAMPLE 1

The bactericide contemplated by this invention is perillyl alcohol which was studied for bactericidal activity against bacteria and yeasts. The organisms tested included the bacteria: *Staphylococcus aureus* ATCC 25923, *Staphylococuus aureus* 37, which is penicillin resistant, *Staphylococcus aureus* 39, which is methicillin resistant; the three toxic shock causing organisms *Staphylococcus aureus* 52T, *Staphylococcus aureus* 53T, and *Staphylococcus aureus* 54T; *Staphylococcus epidermidis* 10, *Streptococcus mutans* which causes dental plaque, *Streptococcus faecalis* 15, *Bacillus subtilis* ATCC 6633, *Escherichia coli*, *Xanthomonas campestris* pv *vesicatoria*, a plant pathogen, *Salmonella* 14 (para B), *Pseudomonas aeriginosa* ATCC 115, and *Pseudomonas cepacia* GM 36; *Mycobacteria fortuitum* ATCC 6841, an acid fast pathogen, and the yeast: *Candida albicans*, a common cause of skin, mouth, and vaginal infections. The minimal bactericidal concentration of perillyl alcohol needed to kill these bacteria and yeasts is outlined in Table B. below. The perillyl alcohol used in the tests was obtained from Aldrich Chemical Company, Milwaukee, Wis., Catalogue Number 21,839-1 and Lot Number 2029 JE-KE.

TABLE B

BACTERICIDAL ACTIVITY OF PERILLYL ALCOHOL

| ORGANISM | BACTERICIDAL CONCENTRATION AT | | |
|---|---|---|---|
| | 10 Min | 60 Min | 24 Hours |
| A. BACTERIA | | | |
| 1. *Staphylococcus aureus* ATCC 25923 | 0.06 | 0.0012 | 0.0012 |
| 2. *Staphylococcus aureus* 37 | 0.06 | 0.02 | 0.005 |
| 3. *Staphylococcus aureus* 39 | 0.06 | 0.0025 | 0.0025 |
| 4. *Staphylococcus aureus* 52T* | 0.06 | 0.0025 | 0.0012 |
| 5. *Staphylococcus aureus* 53T* | 0.06 | 0.02 | 0.005 |
| 6. *Staphylococcus aureus* 54T* | 0.06 | 0.02 | 0.0012 |
| 7. *Staphylococcus epidermidis* 10 | >0.10 | 0.01 | 0.0025 |
| 8. *Streptococcus mutans* | 0.06 | 0.005 | 0.0012 |
| 9. *Streptococcus faecalis* 15 | 0.10 | 0.01 | 0.0025 |
| 10. *Streptococcus pyogenes* 1 | 0.005 | 0.005 | 0.0025 |
| 11. *Bacillus subtilis* ATCC 6633 | 0.10 | 0.10 | 0.01 |
| 12. *Escherichia coli* 7 | 0.0025 | 0.0012 | 0.0012 |
| 13. *Xanthomonas campestris* pv *vesicatoria* | 0.0025 | 0.0025 | 0.0025 |
| 14. *Salmonella* 14 (para B) | 0.0025 | 0.0025 | 0.0025 |
| 15. *Pseudomonas aeriginosa* 115 | 0.01 | 0.005 | 0.005 |
| 16. *Pseudomonas cepacia* GM 36 | 0.005 | 0.0025 | 0.0025 |
| 17. *Mycobacteria fortuitum* ATCC 6841 | 0.01 | 0.005 | 0.0025 |
| B. YEAST | | | |
| 1. *Candida albicans* | 0.005 | 0.0025 | 0.0025 |

*Indicates strains of *Staphylococcus aureus* associated with toxic shock

The standard assay used to test the bactericidal activity of perillyl alcohol against the different bacteria and yeast was as follows: various dilutions of perillyl alcohol were prepared in an appropriate broth medium for each test strain. An inoculum of $10^6$ colony-forming units (CFU/ml) was used. Each test was incubated at the proper temperature for each organism and subcultured (0.01 ml) at 10 minutes, 60 minutes, and 24 hours onto agar media free of perillyl alcohol. Results were expressed as the bactericidal concentration, i.e. the lowest concentration of perillyl alcohol (ml perillyl alcohol/total ml of test) killing at least 99.99% of the bacterial inoculum.

The activity of perillyl alcohol against Mycobacteria was assayed using undiluted oil, and oil diluted up to 1:8000 in Proskauer Beck liquid medium. Each test was inoculated with $10^6$ CFU/ml of Mycobacteria and incubated at 37° C. in 7% $CO_2$ in air. At various time intervals, each test was shaken vigorously and a 0.01 aliquot removed. This was subcultured onto Dubos oleic acid-albumin agar plates to determine the number of viable Mycobacteria remaining. Each test was sampled in this fashion after incubation for 10 minutes, 60 minutes, 24 hours, 1, 2, 3, and 4 weeks. The bacterial concentration was defined as the lowest concentration of oil killing at least 99.9% of the original inoculum.

Details of each assay are presented in Table C which follows.

TABLE C

Test conditions used to assay the bactericidal activity of Perillyl Alcohol:

| ORGANISM | BROTH MEDIUM | SUB-CULTURE AGAR MEDIUM | INCUBATION CONDITIONS |
|---|---|---|---|
| 1. Staphylococcus, Bacillus, and Enterobacteriaceae | Mueller-Hinton | 5% sheep blood | air at 37° C. |
| 2. Streptococcus | Todd-Hewitt | 5% sheep blood | 10% $CO_2$ in air at 37° C. |
| 3. Xanthomas | Mueller-Hinton | blood agar | air at 37° C. |
| 4. Mycobacteria | Proskauer Beck liquid medium | Dubos oleic acid-albumin agar | 7% $CO_2$ at 37° C. |
| 5. *Candida albicans* | Sabouraud dextrose | 5% sheep blood | air at 37° C. |

EXAMPLE 2

PLAQUE INHIBITION BY PERILLYL ALCOHOL

Perillyl alcohol was effective in killing all the different strains of bacteria and yeast tested, including Streptococcus mutans. It's ability to kill Streptococcus mutans makes it very effective in inhibiting plaque formation on surfaces. The best method of demonstrating the plaque inhibiting properties of a substance is by the Streptococcus Mutans Plaque Inhibition Test, which is explained below. In the laboratory small glass rods were immersed in perillyl alcohol and quickly removed simulating the painting or rinsing of the teeth with perillyl alcohol. The glass rods were allowed to dry by hanging to allow any excess non-adherent or excess amount of the perillyl alcohol to drip off as would be expected to occur when excess is applied to the teeth. The amount which adhered to the glass rods was tested for its antiplaque activity against Streptococcus mutans simulating the application of perillyl alcohol to the teeth and then the antiplaque activity of the perillyl alcohol remaining on the teeth was determined. As expected, the perillyl alcohol which remained adherent to the glass rods showed excellent antiplaque activity by killing Streptococcus mutans. This strongly supports the finding that perillyl alcohol can be tasted in the mouth for 3-4 hours after only drops are applied to the teeth and are not removed by saliva. It is this adherence to the teeth that gives prolonged contact with Streptococcus mutans, the etiologic agent which causes plaque, and makes perillyl alcohol so effective in inhibiting plaque formation on teeth.

It is recognized that plaque has different degrees of adherence to teeth according to the quantity and quality of the substances which are incorporated in the plaque. As plaque is removed from the teeth, Streptococcus mutans, the etiologic agent which causes plaque can be cultured from the plaque. Vigorous rinsing of the glass rods to remove plaque is simulates the brushing of teeth to remove plaque. Lightly adherent plaque is removed with the first wash, and more strongly adherent plaque is removed with the second wash, and very strongly adherent plaque is removed only by the third wash. The number of colonies of Streptococcus mutans which can be cultured from each washing corresponds to the amount of plaque removed at each washing, and when no Streptococcus mutans remains on the glass rods after three rinses, it shows that plaque is not present and proves an effective antiplaque agent (or antimicrobial) has been used.

This laboratory assay is generally accepted by oral microbiologists as most nearly simulating the deposition of *Streptococcus mutans* generated plaque on teeth and allows a method for testing the inhibition of plaque formation on teeth. Table D below shows the antiplaque activity of perillyl alcohol and compares its plaque inhibiting activity with controls of water and glycerol.

TABLE D

Effect of various agents on the in vitro plaque development by *Streptococcus mutans*

| Test Agent | Colony Forming Units of S. mutans per ml. in: | | | | Growth of S. mutans on Subculture of Rod to: | |
|---|---|---|---|---|---|---|
| | TH Broth | Wash #1 | Wash #2 | Wash #3 | Blood Agar | TH Broth |
| $H_2O$ Control | $6.1 \times 10^6$ | $3.4 \times 10^6$ | $2.5 \times 10^5$ | $9.2 \times 10^4$ | $4+^1$ | $1+$ |
| Glycerol Control | $3.2 \times 10^7$ | $6.6 \times 10^6$ | $3.7 \times 10^5$ | $3.1 \times 10^4$ | $4+$ | $1+$ |
| Perillyl Alcohol | | | | | | |
| 100% | $2.1 \times 10^3$ | $2.0 \times 10^1$ | 0 | 0 | $NG^2$ | NG |
| 50% | $3.1 \times 10^4$ | $2.0 \times 10^1$ | 0 | 0 | NG | NG |
| 25% | $2.6 \times 10^3$ | 0 | 0 | 0 | NG | NG |
| 12.5% | $1.4 \times 10^7$ | $1.7 \times 10^5$ | $5.0 \times 10^2$ | $1.8 \times 10^1$ | $1+^3$ | $1+$ |

[1] $4+$ = heavy growth
[2] NG = no growth
[3] $1+$ = light growth

The method to determine the in vitro plaque development by *Streptococcus mutans* was as follows: small glass rods (2 mm diameter, 1 cm length) were immersed in distilled water, glycerol, and perillyl alcohol diluted in glycerol, after which they were removed and allowed to dry by hanging on sterile floss overnight. *Streptococcus mutans* ($10^4$ CFU/ml) was inoculated into individual sterile tubes containing 4.5 ml Todd-Hewitt broth with 5% sucrose, after which the rods were suspended in the medium. After 24 hours incubation at 37° C. in 10% $CO_2$ in air, the rods were removed and the number of CFU/ml in the broth was determined by dilution plate counts. The rods were dried on sterile filter paper and placed in a sterile tube to which 3 ml of physiologic saline was added. Each tube was mixed vigorously (Vortex Genie Mixer, Scientific Products, Evanston, Ill.) for 5 seconds, the saline was removed, and the CFU/ml were determined by dilution plate counts (wash #1). Each rod was dried again on sterile filter paper, was placed in a second sterile tube to which 3 ml of physiologic saline was added and mixed vigorously (Vortex) for 30 seconds. The CFU/ml in this second saline (wash #2) was determined by dilution plate counts. After a third drying on filter paper, each rod was placed in a third tube, to which 3 ml of physiologic saline was added and the tube was vigorously mixed (Vortex) for three minutes. The CFU/ml in this third saline (wash #3) was determined by dilution plate counts. After a fourth drying, each rod was rolled on the surface of a 5% sheep blood agar plate and was then placed in a tube of 9ml Todd-Hewitt broth after which the blood agar plate and the broth were incubated 24 hours at 37° C. in 10% $CO_2$ in air. Results of this assay were interpreted as follows: if organisms were recovered from wash #1 only this was considered weak attachment of the organisms to the rod. Moderately attached organisms were recovered in wash #2 and strongly attached organisms were recovered in wash #3. Growth on the blood agar or Todd-Hewitt broth subcultures was considered to be due to very strongly attached organisms which were not killed by the antimicrobial on the rods. Results of this assay are demonstrated in Table D above. It should be noted (in Table D) that the highest dilution of perillyl alcohol to completely prevent strong attached organisms and very strongly attached organisms was a 25% solution (vol/final vol) of perillyl alcohol in glycerol.

EXAMPLE 3

Formulations Which Incorporate Perillyl Alcohol as a Compound to Kill Bacteria and Yeasts The following formulations are prepatred using perillyl alcohol in liquids, gels, soaps, paints, pastes, creams, ointments, suppositories, tampons, aerosols, and emulsions. When bacteria and yeasts are treated with perillyl alcohol containing formulations, the formulations kill or prevent the growth of bacteria and yeasts.

| CHEMICAL | % OF TOTAL | RANGE | ACTION |
|---|---|---|---|
| A. LIQUIDS | | | |
| 1. SOLUTIONS OR SPRAYS | | | |
| a. Perillyl Alcohol | 6.0% | 0.1-50% | bactericide |
| Corn Oil | 94.0% | 50-99.9% | diluent |
| | 100.0% | | |
| b. Perillyl Alcohol | 1.0% | 0.1-50% | bactericide |
| Ethyl Alcohol | 99.0% | 50-99.9% | diluent |
| | 100.0% | | |
| 2. MOUTHWASH | | | |
| a. Perillyl Alcohol | 50.0% | 0.1-50% | antiyeast agent |
| Flavor | 2.0% | 1-5% | flavor |
| Ethyl Alcohol | 48.0% | 45-98.9% | diluent |
| | 100.0% | | |
| B. DENTIFRICE | | | |
| 1. LIQUID | | | |
| Liquid soap concentrate | 5.0% | 2-10% | surfactant |
| Saccharin | 0.2% | 0.1-1.0% | flavor |
| Clove Oil | 1.0% | 0.5-3.0% | flavor |
| Cinnamon Oil | 0.5% | 0.5-3.0% | flavor |
| Peppermint Oil | 0.5% | 0.5-3.0% | flavor |
| Ethyl Alcohol | 42.6% | 29.5-95.3% | diluent |
| Color | 0.2% | 0.1-0.5% | color |
| Perillyl Alcohol | 50.0% | 1-50% | bactericide |
| | 100.0% | | |
| 2. GEL | | | |
| Sodium monofluorophosphate | 0.8% | 0.5-1.5% | antiplaque |
| Perillyl Alcohol | 50.0% | 1-50% | bactericide |
| Hydrated silica xerogel | 10.0% | 8-15% | abrasive |
| Hydrated thickening silica | 8.5% | 5-10% | binder |
| Sorbitol 70% solution | 18.8% | 5-73.3% | humectant |
| Polyethylene glycol 32 | 5.0% | 3-7% | bodying agent |
| Sodium lauryl sulfate | 1.5% | 1-2% | surfactant |

| CHEMICAL | % OF TOTAL | RANGE | ACTION |
|---|---|---|---|
| Carboxymethyl cellulose gum | 1.0% | 0.5-2% | binder |
| S D alcohol | 1.0% | 0.5-2% | stabilizer |
| Flavor | 3.0% | 2-4% | flavor |
| Saccharin | 0.2% | 0.1-0.5% | flavor |
| F D & C Green #3 | 0.1% | 0.1-0.5% | color |
| F D & C Yellow #10 | 0.1% | 0.1-0.5% | color |
| | 100.0% | | |

3. PASTE

| CHEMICAL | % OF TOTAL | RANGE | ACTION |
|---|---|---|---|
| Sodium monofluorophosphate | 0.8% | 0.5-1.5% | antiplaque |
| Perillyl Alcohol | 50.0% | 1-50% | bactericide |
| Dicalcium phosphate dihydrate | 22.0% | 20.4-30% | abrasive |
| Water | 16.0% | 11.1-69.5% | diluent |
| Glycerine | 5.1% | 4.5-12.5% | bodying agent |
| Flavor | 2.0% | 2-3% | flavor |
| Sodium lauryl sulfate | 1.5% | 1-2% | surfactant |
| Carboxymethyl cellulose gum | 1.4% | 0.5-2.0% | binder |
| Tetrasodium pyrophosphate | 1.0% | 0.5-2.0% | binder |
| Sodium saccharin | 0.2% | 0.1-0.5% | flavor |
| | 100.0% | | |

C. OINTMENTS & SUPPOSITORIES WITH AND WITHOUT HYDROCORTISONE

1. OINTMENT WITH HYDROCORTISONE

| CHEMICAL | % OF TOTAL | RANGE | ACTION |
|---|---|---|---|
| Perillyl Alcohol | 1.0% | 0.1-15.0% | bactericide |
| Polyethylene glycol 3350 | 59.0% | 48.5-59.7% | bodying agent & emulsifier |
| Polyethylene glycol 400 | 39.0% | 31.5-39.7% | bodying agent & emulsifier |
| Hydrocortisone | 1.0% | 0.5-5.0% | anti-inflammatory |
| | 100.0% | | |

2. OINTMENT WITHOUT HYDROCORTISONE

| CHEMICAL | % OF TOTAL | RANGE | ACTION |
|---|---|---|---|
| Perillyl Alcohol | 1.0% | 0.1-15.0% | Antiyeast agent |
| Polyethylene glycol 3350 | 59.5% | 51.0-59.95% | bodying agent & emulsifier |
| Polyethylene glycol 400 | 39.5% | 34.0-39.95% | bodying agent & emulsifier |
| | 100.0% | | |

3. SUPPOSITORY WITHOUT HYDROCORTISONE

| CHEMICAL | % OF TOTAL | RANGE | ACTION |
|---|---|---|---|
| Perillyl Alcohol | 6.0% | 0.1-15% | bactericide |
| Polyethylene glycol 1000 | 56.5% | 51.0-59.95% | bodying agent & emulsifier |
| Polyethylene glycol 3350 | 37.5% | 34.0-39.95% | bodying agent & emulsifier |
| | 100.0% | | |

4. SUPPOSITORY WITH HYDROCORTISONE

| CHEMICAL | % OF TOTAL | RANGE | ACTION |
|---|---|---|---|
| Perillyl Alcohol | 1.0% | 0.1-15% | antiyeast agent |
| Polyethylene glycol 1000 | 74.0% | 60.0-75.2% | bodying agent & emulsifier |
| Polyethylene glycol 3350 | 24.0% | 20.0-24.2% | bodying agent & emulsifier |
| Hydrocortisone | 1.0% | 0.5-5.0% | anti-inflammatory |
| | 100.0% | | |

D. CREAMS WITHOUT HYDROCORTISONE

| CHEMICAL | % OF TOTAL | RANGE | ACTION |
|---|---|---|---|
| 1. Perillyl Alcohol | 6.0% | 0.1-15.0% | bactericide |
| Cetyl alcohol | 15.0% | 12.0-18.0% | thickener |
| Arlacel 165** | 5.0% | 3.5-7.5% | emulsifier |
| Sorbitol 70% solution | 5.0% | 3.5-8.0% | humectant |
| Water | 69.0% | 51.5-80.9% | diluent |
| | 100.0% | | |
| 2. Perillyl Alcohol | 1.0% | 0.1-15.0% | antiyeast agent |
| Spermaceti wax | 12.5% | 10.0-15.0% | thickener |
| Sorbitan monostearate* | 10.0% | 7.5-12.5% | emulsifier |
| Polyethylene 20 Sorbitan monostearate* | 6.0% | 4.0-8.0% | emulsifier |
| Water | 70.5% | 49.5-78.4% | diluent |
| | 100.0% | | |

E. CREAMS WITH HYDROCORTISONE

| CHEMICAL | % OF TOTAL | RANGE | ACTION |
|---|---|---|---|
| 1. Perillyl Alcohol | 1.0% | 0.1-15.0% | antiyeast agent |
| Cetyl alcohol | 15.0% | 12.0-18.0% | thickener |
| Arlacel 165** | 5.0% | 3.5-7.5% | emulsifier |
| Sorbitol 70% solution | 5.0% | 3.5-8.0% | humectant |
| Hydrocortisone | 1.0% | 0.5-5.0% | anti-inflammatory |
| Water | 73.0% | 46.5-80.4% | diluent |
| | 100.0% | | |

*Croda, Inc., 51 Madison Ave., New York, New York 10010
**Glycerol monostearate and polyoxyethylene stearate ICI of America (Formerly Atlas Chemical Industries), Wilmington, Delaware 19899

F. TAMPONS

| CHEMICAL | % OF TOTAL | RANGE | ACTION |
|---|---|---|---|
| 1. Perillyl Alcohol 2 cc 2 Gm | 8% | 1-15% | bactericide |
| Tampon 23 Gm | 92% | 85-99% | reservoir for bactericide |
| | 100% | | |

G. AEROSOLS WITHOUT HYDROCORTISONE

| CHEMICAL | % OF TOTAL | RANGE | ACTION |
|---|---|---|---|
| 1. Perillyl Alcohol | 6.0% | 0.5-50% | bactericide |
| Ethyl alcohol | 94.0% | 50-99.5% | diluent |
| | 100.0% | | |
| Pressurized nitrogen propellant at 100-125 psig | | | |
| 2. Perillyl Alcohol | 10.0% | 0.5-50.0% | antiyeast agent |
| Soybean Oil | 90.0% | 50.0-99.5% | diluent |
| | 100.0% | | |
| Pressurized nitrogen propellant at 100-125 psig | | | |

H. AEROSOL WITH HYDROCORTISONE

| CHEMICAL | % OF TOTAL | RANGE | ACTION |
|---|---|---|---|
| 1. Perillyl Alcohol | 6.0% | 0.5-50% | bactericide |
| Soybean oil | 93.0% | 45-99.0% | diluent |
| Hydrocortisone | 1.0% | 0.5-5.0% | anti-inflammatory |
| | 100.0% | | |
| Pressurized nitrogen propellant at 100-125 psig | | | |

I. OIL IN WATER EMULSION

| CHEMICAL | % OF TOTAL | RANGE | ACTION |
|---|---|---|---|
| 1. Perillyl Alcohol | 0.1% | 0.1-50% | antiyeast agent |
| 2. Corn oil | 10.0% | 10-15% | oil |
| Arlacel 40** | 2.0% | 1-3% | emulsifier |
| Tween 40 | 3.0% | 2-4% | emulsifier |
| 3. Water | 84.9% | 28-86.9% | diluent |
| | 100.0% | | |

Heat 2 to 70° C. Heat 3 to 72° C. Add 3 to 2 with continuous agitation. When 3 and 2 cool to 40° C., add 1 with continuous agitation until room temperature is reached.

| CHEMICAL | % OF TOTAL | RANGE | ACTION |
|---|---|---|---|
| J. OIL IN WATER EMULSION WITH SOAP (BACTERICIDAL SOAP) | | | |
| 1. Perillyl Alcohol | 10.0% | 0.1-25% | bactericide |
| 2. Corn oil | 21.0% | 20.0-40.0% | oil |
| Arlacel 40** | 2.0% | 1.0-3.0% | emulsifier |
| Tween 40 | 3.0% | 2.0-4.0% | emulsifier |
| Liquid soap concentrate | 3.5% | 2.5-5.0% | surfactant |
| 3. Water | 60.5% | 23-74.4% | diluent |
| | 100.0% | | |

Heat 2 to 70° C. Heat 3 to 72° C. Add 3 to 2 with continuous agitation. When 3 and 2 cool to 40° C., add 1 with continuous agitation until room temperature is reached.

| CHEMICAL | % OF TOTAL | RANGE | ACTION |
|---|---|---|---|
| K. WATER IN OIL EMULSION | | | |
| 1. Perillyl Alcohol | 1.0% | 0.1-25% | antiyeast agent |
| 2. Arlacel 186** | 3.0% | 2.0-4.0% | emulsifier |
| Soybean oil | 15.0% | 10.0-25.0% | oil |
| Ceresin wax | 0.5% | 0.3-0.6% | thickener |
| Beeswax | 0.5% | 0.3-0.6% | thickener |
| Tween 80 | 0.5% | 0.3-0.6% | emulsifier |
| 3. Water | 79.5% | 44.2-87.0% | diluent |
| | 100.0% | | |

Heat 2 to 70° C. Heat 3 to 72° C. Add 3 to 2 with continuous agitation. When 3 and 2 cool to 40° C., add 1 with continuous agitation until room temperature is reached.

| CHEMICAL | % OF TOTAL | RANGE | ACTION |
|---|---|---|---|
| L. PAINT | | | |
| 1. ENAMEL | | | |
| Perillyl Alcohol | 1.00% | 1-10% | bactericide |
| Titanium dioxide | 14.91% | 12-16% | pigment |
| Calcium carbonate | 29.83% | 25-35% | pigment |
| Silicate | 4.81% | 3-6% | pigment |
| Soya alkyd resin | 25.72% | 22-28% | pigment (binder) |
| Mineral spirits | 23.73% | 5-37% | solvent (thinner) |
| | 100.0% | | |
| 2. LATEX | | | |
| Perillyl Alcohol | 1.00% | 1-10% | antiyeast |
| Titanium dioxide | 10.76% | 8-12% | pigment |
| Silicate | 12.91% | 10-16% | pigment |
| Calcium carbonate | 20.91% | 15-25% | pigment |
| Vinyl acrylic resin solids | 12.22% | 10-16% | vehicle (binder) |
| Glycol | 8.30% | 6-10% | solvent (thinner) |
| Water | 34.00% | 12-50% | solvent (thinner) |
| | 100.00% | | |

While only certain preferred embodiments of this invention have been shown and described by way of illustration, many modifications will occur to those skilled in the art and it is, therefore, desired that it be understood that it is intended herein, to cover all such modifications that fall within the true spirit and scope of this invention.

We claim:

1. A method of killing bacteria comprising: treating bacteria in its habitat with bactericidal concentrations of perillyl alcohol.

2. The method of claim 1 wherein said bacteria are selected from a group consisting of *Staphylococcus, Bacillus, Enterobacteriaceae, Streptococcus, Xanthomonas,* and *Mycobacteria.*

3. A method of killing yeasts consisting of: treating yeasts in their habitat with an effective concentration of perillyl alcohol to kill said yeasts.

* * * * *